(12) United States Patent
Walters et al.

(10) Patent No.: US 12,402,876 B2
(45) Date of Patent: *Sep. 2, 2025

(54) RELEASABLE ELONGATED ASSEMBLY

(71) Applicant: Teleflex Life Sciences LLC, Wilmington, DE (US)

(72) Inventors: Greg A. Walters, Exton, PA (US); Michael Dotsey, Chester Springs, PA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/663,982

(22) Filed: May 14, 2024

(65) Prior Publication Data

US 2024/0293117 A1    Sep. 5, 2024

Related U.S. Application Data

(63) Continuation of application No. 17/135,147, filed on Dec. 28, 2020, now Pat. No. 11,998,189, which is a
(Continued)

(51) Int. Cl.
*A61F 5/00* (2006.01)
*A61B 17/00* (2006.01)
(Continued)

(52) U.S. Cl.
CPC .... *A61B 17/06166* (2013.01); *A61B 17/0487* (2013.01); *A61B 2017/00336* (2013.01);
(Continued)

(58) Field of Classification Search
CPC .... A61B 2017/0474; A61B 2017/0425; A61B 17/04; A61B 17/0057; A61B 2017/0475;
(Continued)

(56) References Cited

U.S. PATENT DOCUMENTS

| 2,012,776 A | 8/1935 | Albert |
| 2,840,873 A * | 7/1958 | Meier ............. F16G 11/14 403/17 |

(Continued)

FOREIGN PATENT DOCUMENTS

| EP | 2313013 A1 | 4/2011 |
| WO | 9311825 A1 | 6/1993 |
| WO | 2008109394 A2 | 9/2008 |

OTHER PUBLICATIONS

International Search Report and Written Opinion issued in International Application No. PCT/US2017/031268, mailed on Jul. 21, 2017, 16 pages.

(Continued)

*Primary Examiner* — Shaun L David
*Assistant Examiner* — Mitchell Brian Hoag
(74) *Attorney, Agent, or Firm* — Dorsey & Whitney LLP

(57) ABSTRACT

A releasable elongated assembly includes a release member having a length and an opening that extends along the length. The releasable elongated assembly includes a first elongated element having a first coupling member disposed in the opening and a second elongated element having a second coupling member disposed in the opening opposite the first coupling member along the length. The first and second elongated elements are interlaced with each other in the opening at a location between the first coupling member and the second coupling member such that the first and second elongated elements are attached to each other. The release member is moveable from a first position where the first and second coupling members are captured in the opening to a second position where the first and second coupling members are released from the opening so as to detach the first and second elongated elements from each other.

20 Claims, 4 Drawing Sheets

Related U.S. Application Data continuation of application No. 16/098,578, filed as application No. PCT/US2017/031268 on May 5, 2017, now Pat. No. 10,905,414.

(60) Provisional application No. 62/332,347, filed on May 5, 2016.

(51) Int. Cl.
*A61B 17/04* (2006.01)
*A61B 17/06* (2006.01)
*A61B 17/12* (2006.01)

(52) U.S. Cl.
CPC ..... *A61B 2017/00663* (2013.01); *A61B 17/04* (2013.01); *A61B 17/0469* (2013.01); *A61B 2017/047* (2013.01); *A61B 2017/0474* (2013.01); *A61B 2017/0477* (2013.01); *A61B 17/0483* (2013.01); *A61B 17/12* (2013.01); *A61B 17/12022* (2013.01); *A61F 5/0083* (2013.01)

(58) Field of Classification Search
CPC .... A61B 2017/0433; A61B 2017/0448; A61B 2017/0477; A61B 17/0469; A61B 17/0483; A61B 2017/00663; A61B 2017/047; A61B 2017/00575; A61B 2017/00579; A61B 2017/00584; A61B 2017/00588; A61B 2017/0065; A61B 2017/00654; A61B 2017/00637; A61B 2017/00641; A61B 2017/00623; A61B 2017/00592; A61B 2017/00601; A61B 2017/00606; A61B 2017/0061; A61B 2017/00615; A61B 2017/00619; A61B 2017/00628; A61B 2017/00646; A61B 2017/00659; A61F 2/0811; A61F 5/0083; A61F 2002/0817; A61F 2002/0823; A61F 2002/0829; A61F 2002/0835; A61F 2002/0841; A61F 2002/0847; A61F 2002/0852; A61F 2002/0858; A61F 2002/0864; A61F 2002/087
USPC ......................................................... 606/151
See application file for complete search history.

(56) References Cited

U.S. PATENT DOCUMENTS

| | | | | |
|---|---|---|---|---|
| 4,235,238 | A | | 11/1980 | Ogiu et al. |
| 4,375,118 | A | | 3/1983 | Saylor |
| 4,950,285 | A | * | 8/1990 | Wilk ..................... A61B 17/06 24/17 AP |
| 5,123,913 | A | * | 6/1992 | Wilk ................. A61B 17/12009 24/17 AP |
| 5,810,845 | A | * | 9/1998 | Yoon ................ A61B 17/12013 606/151 |
| 8,696,688 | B2 | * | 4/2014 | Stone .................. A61B 17/0482 606/144 |
| 9,681,864 | B1 | * | 6/2017 | Gammie ............ A61B 17/0487 |
| 10,188,537 | B2 | | 1/2019 | Lim et al. |
| 10,905,414 | B2 | | 2/2021 | Walters et al. |
| 11,304,689 | B2 | | 4/2022 | Miller et al. |
| 11,684,468 | B2 | | 6/2023 | Hernandez |
| 11,998,189 | B2 | | 6/2024 | Walters et al. |
| 2002/0095165 | A1 | | 7/2002 | Chan |
| 2005/0043756 | A1 | * | 2/2005 | Lavelle ................. A61B 17/221 606/200 |
| 2006/0111205 | A1 | * | 5/2006 | Abel ................... A63B 69/0086 473/576 |
| 2006/0264975 | A1 | * | 11/2006 | Pipenhagen ....... A61B 17/0057 606/144 |
| 2007/0083236 | A1 | | 4/2007 | Sikora et al. |
| 2007/0261211 | A1 | | 11/2007 | Muchanic |
| 2008/0051831 | A1 | * | 2/2008 | Deal ................ A61B 17/12099 606/213 |
| 2008/0221654 | A1 | | 9/2008 | Buiser et al. |
| 2009/0171387 | A1 | | 7/2009 | Pipenhagen et al. |
| 2009/0216266 | A1 | * | 8/2009 | Maruyama ......... A61B 17/0057 606/151 |
| 2010/0094401 | A1 | | 4/2010 | Kolbel et al. |
| 2011/0218613 | A1 | * | 9/2011 | Leopold .................... A61F 2/95 623/1.2 |
| 2011/0282385 | A1 | * | 11/2011 | Gilson ............ A61B 17/06066 606/224 |
| 2011/0301638 | A1 | | 12/2011 | Walters |
| 2012/0191133 | A1 | * | 7/2012 | Ferree ................ A61B 17/0469 606/228 |
| 2013/0158598 | A1 | * | 6/2013 | Lizardi ............. A61B 17/0401 606/232 |
| 2013/0190819 | A1 | * | 7/2013 | Norton .............. A61B 17/0401 606/232 |
| 2013/0253574 | A1 | * | 9/2013 | Catanese, III ......... A61B 17/42 606/201 |
| 2014/0336672 | A1 | | 11/2014 | Walters et al. |
| 2016/0302789 | A1 | | 10/2016 | Hirotsuka et al. |
| 2016/0310116 | A1 | * | 10/2016 | Walters ............. A61B 17/0469 |
| 2016/0374655 | A1 | | 12/2016 | Walters et al. |
| 2017/0095259 | A1 | * | 4/2017 | Tompkins ........ A61B 17/12113 |
| 2019/0142418 | A1 | | 5/2019 | Walters et al. |
| 2020/0360009 | A1 | | 11/2020 | Lombardo et al. |
| 2022/0304677 | A1 | * | 9/2022 | Wulc .................. A61B 17/0491 |
| 2025/0049435 | A1 | * | 2/2025 | Tsui ................... A61B 17/0057 |

OTHER PUBLICATIONS

European Search Report mailed May 22, 2024, in European patent application 23218800.3.

* cited by examiner

RELEASABLE ELONGATED ASSEMBLY

CROSS-REFERENCE TO RELATED APPLICATIONS

The present application is a Continuation application of U.S. application Ser. No. 17/135,147, filed Dec. 28, 2020, entitled "Releasable Elongated Assembly," issued as U.S. Pat. No. 11,998,189 on Jun. 4, 2024, which is a continuation of U.S. application Ser. No. 16/098,578, filed Nov. 2, 2018, entitled "Releasable Elongated Assembly," issued as U.S. Pat. No. 10,905,414 on Feb. 2, 2021, which claims the benefit of, priority to, and is a National Phase Application under 35 U.S.C. § 371 of PCT Application No. PCT/US2017/031268, filed May 5, 2017, entitled "Releasable Elongated Assembly," which claims the benefit of, and priority to, U.S. Provisional Application No. 62/332,347, filed May 5, 2016, entitled "Releasable Elongated Assembly." The entire disclosure of each application listed in this paragraph is incorporated herein by reference into the present application.

TECHNICAL FIELD

The present disclosure relates to a releasable elongated assembly.

BACKGROUND

There are a wide range of applications where it is necessary to attach two structures together and have the ability to quickly release them from each other if needed. It is common in surgical, orthopedic, and endovascular procedures to secure sutures using knots, clips, slides or other joining methods. Typically, this requires a working length of suture to fashion the attachment or joining, and following such joining, leaves a length of unused suture that must be trimmed or cut near the joining point. When sutures are secured remotely, the unused end is typically cut remotely using a suture cutter that is often times a separate item that can be expensive or difficult to use.

SUMMARY

There is a need for a releasable suture splice that can be remotely released to avoid the need for remote suture cutting. Accordingly, an embodiment of the present disclosure is a releasable elongated assembly. The releasable elongated assembly includes a release member having a length and an opening that extends along the length. The releasable elongated assembly includes a first elongated element having a first coupling member disposed in the opening and a second elongated element having a second coupling member disposed in the opening opposite the first coupling member along the length. The first elongated element and the second elongated element are interlaced with each other in the opening at a location between the first coupling member and the second coupling member such that the first and second elongated elements are attached to each other. The release member is moveable from a first position where the first and second coupling members are captured in the opening to a second position where one of the first and second coupling members is released from the opening so as to detach the first and second elongated elements from each other.

Another embodiment of the present disclosure is a releasable elongated assembly that is elongate along a longitudinal direction. The releasable elongated assembly includes a release member including an elongate opening that extends along the longitudinal direction. The release member includes a first elongated element having a first coupling member disposed in the elongate opening and a second elongated element having a second coupling member disposed in the elongate opening opposite with respect to the first coupling member along the longitudinal direction. The releasable elongated assembly also includes a releasable joint where the first elongated element and the second elongated element are interlaced with each other in the elongate opening, the releasable joint being disposed between the first coupling member and the second coupling member along the longitudinal direction. The releasable elongated assembly has 1) a first attached configuration where the release member captures the first coupling member, the releasable joint, and the second coupling member so as to prevent release of the first and second elongated elements from each other, and 2) a second released configuration where the release member is moved along the longitudinal direction to release the first and second elongated elements from each other.

Another embodiment of the present disclosure is a suture assembly that is elongate along a longitudinal direction. The suture assembly includes a release member including a lumen that extends along the longitudinal direction. The suture assembly also includes a first suture having a first coupling member disposed in the lumen and a second suture having a second coupling member disposed in the lumen opposite with respect to the first coupling member along the longitudinal direction. The suture assembly also includes a releasable joint where the first suture and the second suture are interlaced with each other in the lumen, the releasable joint being disposed between the first coupling member and the second coupling member along the longitudinal direction. The suture assembly is configured to transition from 1) a first attached configuration where the release member captures the first coupling member, the releasable joint, and the second coupling member so as to prevent release of the first and second sutures from each other, into 2) a second released configuration where the release member is moved along the longitudinal direction to release the first and second sutures from each other.

Another embodiment of the present disclosure is a suture assembly elongate along a longitudinal direction. The suture assembly includes a release member including a lumen that extends along the longitudinal direction. The suture assembly also includes a first suture having a first coupling member disposed in the lumen. The first suture is folded in the lumen to define a first loop adjacent to the first coupling member. The suture assembly also includes a second suture having a second coupling member disposed in the lumen. The second suture is folded in the lumen to define a second loop adjacent to second coupling member. The suture assembly includes a releasable joint where the first loop and the second loop are interlaced with each other in the lumen, the releasable joint being disposed between the first coupling member and the second coupling member. The suture assembly has 1) a first attached configuration where the release member maintains the releasable joint between the first and second coupling members so as to prevent release of the first and second sutures from each other, and 2) a second released configuration where the release member is moved to eject the first and second coupling members from the lumen so as to release the first and second sutures from each other.

DETAILED DESCRIPTION OF ILLUSTRATIVE EMBODIMENTS

Figure 1:
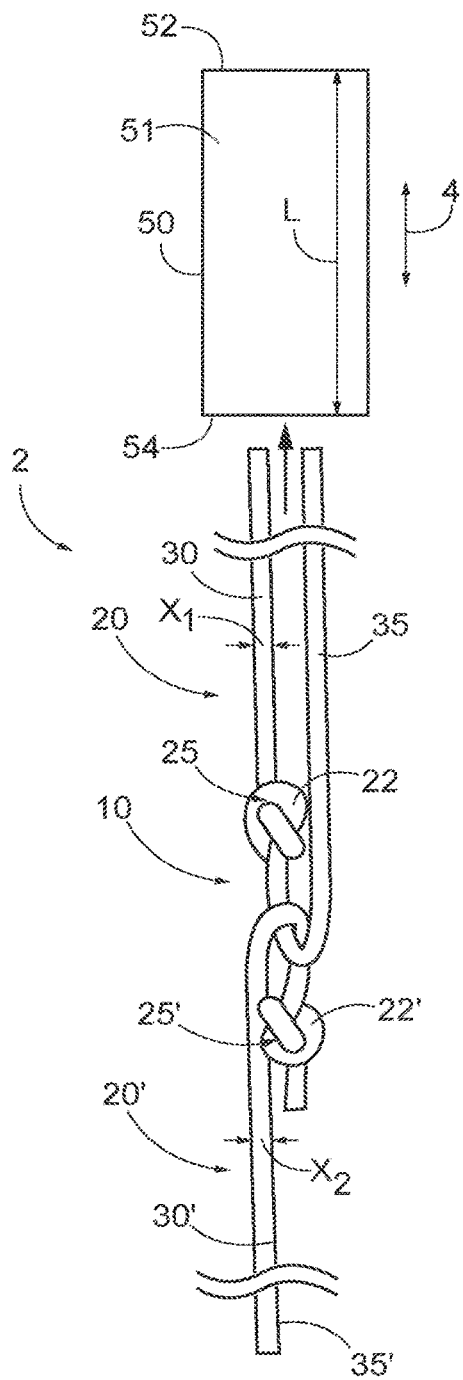
FIG. 1 is a schematic showing a releasable elongated assembly including intertwined coupling ends of two elongated elements disposed with in release member.

Referring to FIGS. 1-5, disclosed is a releasable elongated assembly 2 comprised of a release member 50, a first elongated element 20, and a second elongated element 20' that are overlaid over one another and reside within the release member 50. The first elongated element 20 and the second elongated element 20' has a first coupling member 25 and a second coupling members 25', respectively. The first and second coupling members 25, 25' are intertwined with each other inside an opening 56 of the release member 50. The internal dimension D (FIG. 5) of the release member 50 is sized to allow passage of a single coupling member, but with insufficient clearance to allow the two coupling members 25, 25' to pass one another within the opening 56 of the release member.

The release member 50 together with the intertwined elongated elements 20, 20' form a splice or releasable joint 10. The releasable joint 10 is where the two elongated elements 20, 20' are joined within release member 50 and will support tension along the joined length.

The releasable joint 10 is configured so as to withstand applied tensile forces to the lengths of material due to the tight fit of the coupling members 25, 25' within the opening of the release member 50. Each respective coupling member 25, 25' is prevented from traversing the opposing loop with the other coupling member 25, 25' present in the opening 56. Thus, under a tensile load the joint 10 'jams' in the release member 50 and acts as a useful splice.

Figure 3:
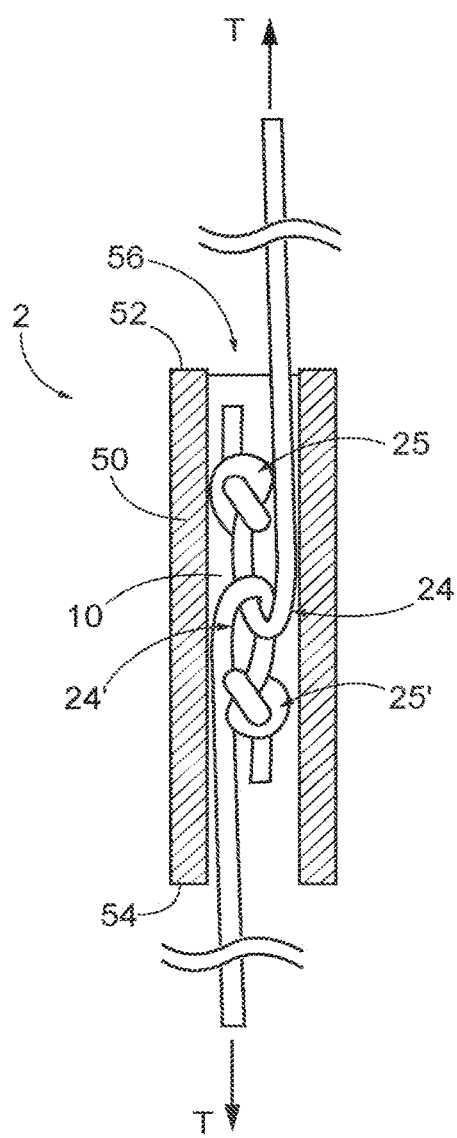
FIG. 3 is a partial sectional view of the releasable elongated assembly shown in FIG. 2, illustrating how the elongated elements are captured within the release member.
Figure 4:
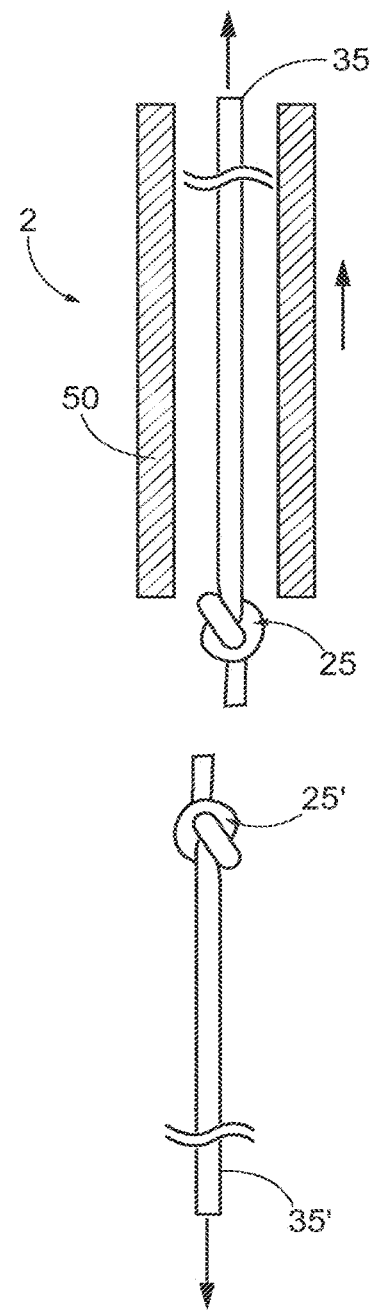
FIG. 4 is a partial sectional view of the releasable elongated assembly shown in FIG. 2, illustrating the release member moved to expose the intertwined coupling ends and allows them to release from each other.

In operation, movement of the release member 50 from a first position over the location of the entwinement of the two coupling members 25, 25', as shown in FIG. 3, into a second position away from the entwinement, as shown in FIG. 4, allows the two coupling members 25, 25' to be released from the release member 50 and the two elongated elements 20, 20' to be released from one another. The first position of the release member 50 shown in FIG. 3 may be referred to as the holding position. The second position of the release member as shown in FIG. 4 may be referred to as the releasing position. Furthermore, the first position may also be considered a first attached configuration where the release member 50 captures the first coupling member 25, the releasable joint 10, and the second coupling member 25' so as to prevent release of the first and second elongated elements 20, 20' from each other. The second position may also be referred to as the second released configuration where the release member 50 is moved along the longitudinal direction to release the first and second elongated elements 20, 20' from each other. Accordingly, the releasable elongated assembly 2 includes first and second elongated elements 20 and 20' that are releasably attached to each other. The embodiment shown in FIG. 1 is configured as a suture assembly with first and second elongated elements in the form of first and second sutures, respectively. It should be appreciated, however, that the releasable assembly 2 can be formed with any elongated length of material as will further explained below.

Continuing with FIGS. 1-5, the release member 50 includes a body 51 that defines a first end 52, a second end 54 opposite to the first end 52 along a longitudinal direction 4, and an opening 56 that extends from the first end 52 to the second end 54 along the longitudinal direction 4. The release member 50 defines a length L that extends from the first end 52 to the second end 54 along the longitudinal direction 4. The release member 50 includes an inner surface 58 and an outer surface 59 opposite the inner surface 59. The inner surface 58 defines the opening 56 and a dimension D of the opening 56 that is perpendicular to the length L. The dimension D of the opening 56 is such that the first and second coupling members 25, 25' are inhibited from moving past each other in the opening 56. The release member 50 is in the form of a hollow cylinder, or tube with an opening 56 that extends through its length L. The opening 56 can be circular, oval, rectilinear (square or rectangular) or any suitable shape. In some embodiments, the opening 56 is an elongated lumen.

Figure 2:
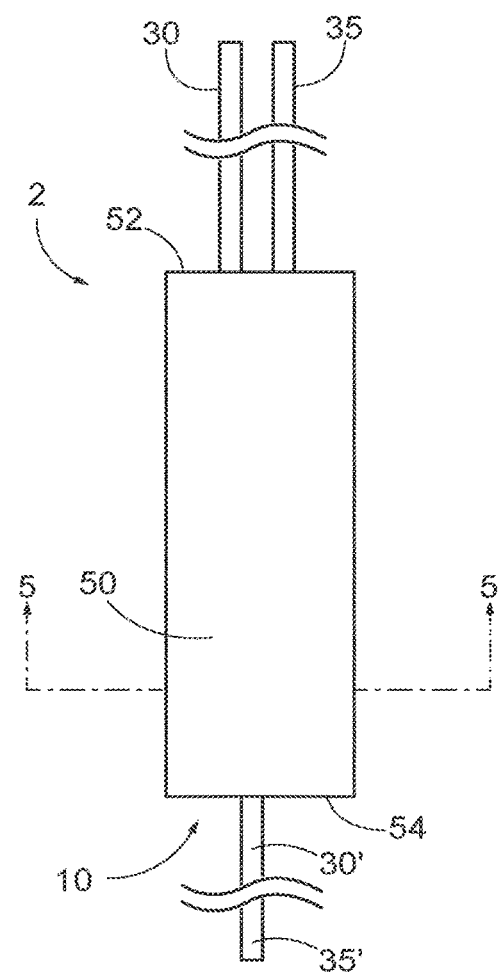
FIG. 2 depicts the releasable assembly shown in FIG. 1, illustrating the release member positioned around the intertwined coupling ends of the elongated elements.

Continuing with FIGS. 1-5, the first and second elongated elements 20 and 20' each include first and second coupling members 25 and 25', respectively. The first elongated element 20 comprises a length of material 30 having opposed ends (only one end 35 shown). As illustrated, the first elongate element has a first terminal end 35 with a coupling member 25 disposed proximate the first terminal end 35. Likewise, the second elongated element 20' comprises a length of material 30' with two opposed ends (only one end 35 shown). As illustrated, the second elongate element 20' has a second terminal end 35' with a second coupling member 25' proximate the second terminal end 35'. However, the coupling members 25, 25' can be disposed at any location along the elongated elements 20, 20' as needed. In one example as illustrated, the first elongated element 20, e.g. the first length of material 30, extends out of the first end 52 of the release member 50, and the second elongated element 20', e.g. the second length of material 30', extends out of the second end 54 of release member 50. The length 30 of material beyond coupling member 25 is utilized together with terminal end 35 to thread the joint 10 through the release member 50 for the purpose of placing the release member 50 over the joint 10, as shown in FIG. 2.

The elongated elements 20, 20' may be any elongated length of material. For example, the elongated elements 20, 20' may be any elongated length of material such as a cord, a rope, a plied strand, a monofilament strand, a multifilament strand, a braid, a wire, twine, band, a cable, a suture, flat strip of materials, or an elongated rigid rod. In one example, the first and second lengths of material 30, 30' forming the elongated elements 20, 20' may be similar.

Alternatively, the first and second lengths of material 30, 30' forming the elongated elements 20, 20' are different. The first and second elongated elements described above are generally flexible materials that can be twisted around each other so as to entwine the coupling members in the release member. Alternately, in one example, one of the elongated elements can be rigid while the other elongated element can be flexible. In such an example, the release of the first and second elongated elements 20, 20' is possible so long as the coupling members 25, 25' can be pass beyond each other once the release member 50 is moved into a releasing position.

Furthermore, in another alternative embodiment, a portion of the first and second elongated elements can be stiff or generally rigid. For instance, the elongated elements comprise a length of material that is flexible while another portion can be rigid or stiff.

Figure 5:
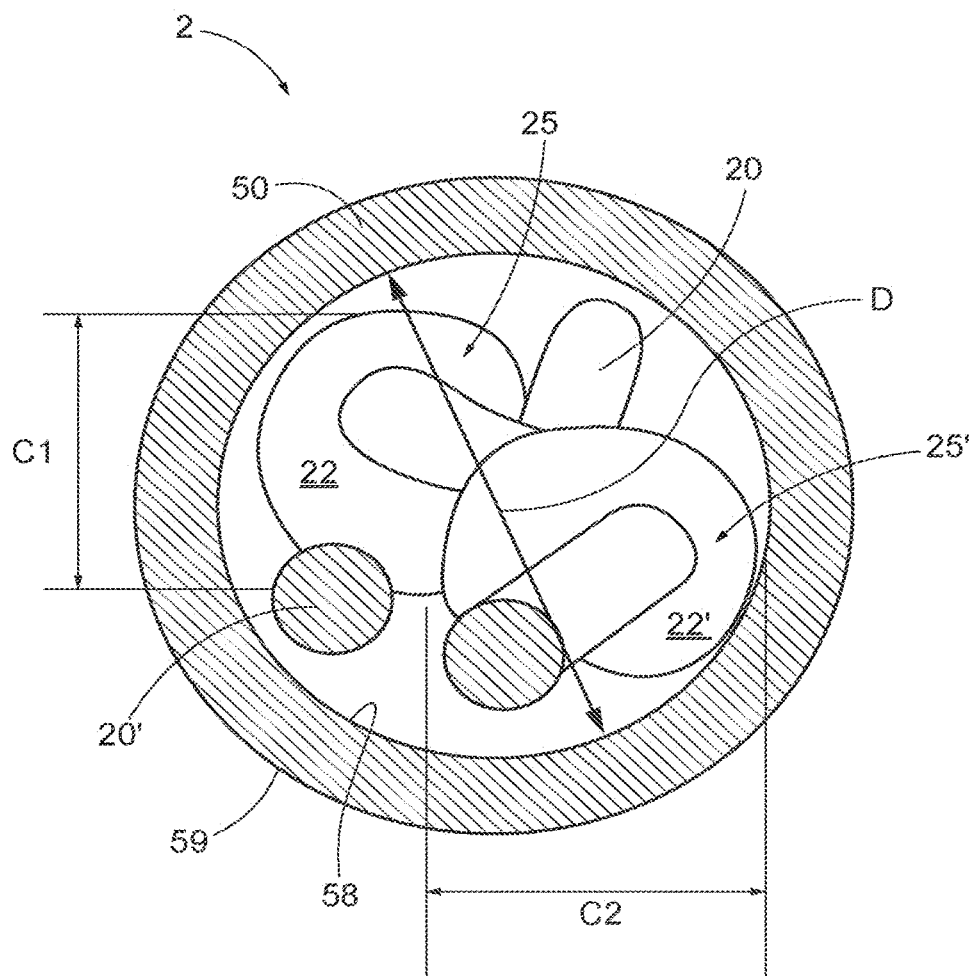
FIG. 5 is a cross-sectional view of the releasable elongated assembly taken along line 5-5 in FIG. 2.

Referring to FIGS. 1-5, the coupling members 25, 25' are designed to entrap each other within the release member 50. The first coupling member 25 includes a first body 22 attached to (or monolithic with) the first elongated element 20 and the second coupling member 25' is a second body 22' attached (or monolithic with) the second elongated element 20'. As best shown in FIGS. 1 and 5, the first coupling member 25 defines a maximum cross-sectional dimension C1 that is greater than a cross-sectional dimension X1 of the first elongated element 20. Likewise, the second coupling member 25' defines a maximum cross-sectional dimension C2 that is greater than a cross-sectional dimension X2 of the second elongated element 20'. The cross-sectional dimension X1 and X2 are perpendicular to a central axis (not shown) of each respective elongated element. Furthermore, the combined maximum cross-sectional dimensions C1 and C2 is \less than the dimension D of the opening 56 of the release member 50. This allows the two coupling members 25, 25' to be entrapped in the release member, inhibiting each from passing by the other.

In accordance with the illustrated embodiment, the coupling members 25, 25' can be knots. For example, the first coupling member 25 is a first knot and the second coupling ember 25' is a second knot. In such an example, the first and second knots are monolithic with the respect to the first and second elongated elements 20 and 20', respectively. In another alternative example, the first and second knots are separate from and attached to the first and second elongated elements 20 and 20', respectively. However, the coupling members any structure or device or structures having a variety of shapes that is generally large than cross-sectional dimension of the elongated elements 20, 20'.

For example, the coupling members 25, 25' can be stiffened sections of the elongated elements or have other configurations as discussed further below. In such an example, the first and second coupling members are first and second rigid elements disposed on the first and second elongated elements. Each elongated element is a length of material and each rigid element is a rigid portion of the length of material.

Figure 6:
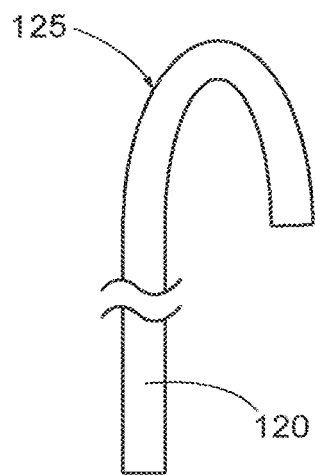
FIG. 6 is a side view of an elongated element and coupling member according to an embodiment of the present disclosure.

In another alternative embodiment, as shown in FIG. 6, the elongated elements can be a rigid rod 120 with its coupling member 125 configured as a hook at the end of the rigid rod 120, e.g., a shepherd's hook. In such an embodiment, the releasable assembly includes a first elongated element configures as a rigid rod and the first coupling member is a hook disposed at the end of the rigid rod. The second elongated element is a second rigid rod and the second coupling member is in the form of a second hook.

Figure 7:
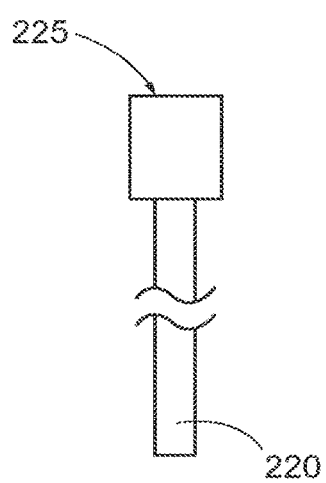
FIG. 7 is a side view of an elongated element and coupling member according to another embodiment of the present disclosure.
Figure 8:
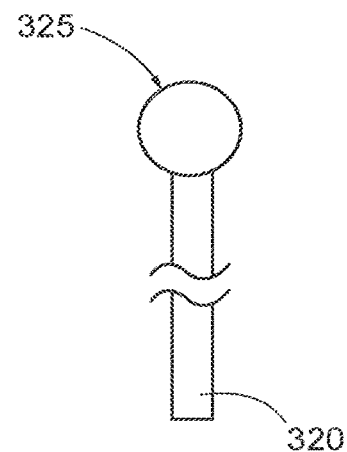
FIG. 8 is a side view of an elongated element and coupling member according to another embodiment of the present disclosure.

In another alternative embodiment, as shown in FIG. 7, the elongated elements 220 has a coupling member 125 configured as an enlarged stiffened member 225. In such an example, the ends of the elongated element 220 can be stiffened so as to define the coupling member. The size of the stiffened portion is greater than the inner dimension D of the opening 56 of the release member 50 so as to maintain its position within the opening of the release member 50 when entwined with another similar elongated element and coupling member.

In another alternative embodiment, as shown in FIG. 7, the elongated element 320 has a coupling member 325 configured a spherical body. However, it should be appreciated that the coupling member can have bodies that define one of a substantially spherical shape, a substantially cylindrical shape, a substantially cuboidal shape, or a substantially ovoidal shape.

As shown in FIGS. 3 and 4, the first and second elongated elements 20 and 20' can be released by moving the release member 50 off or away from the releasable joint 10. Once the release member 50 moves beyond coupling member 25, the elongated elements 20 and 20' effectively fall apart. In operation, the first elongated element 20 is folded in the opening to define a first loop 24 adjacent to the first coupling member 25, and the second elongated element 20', is folded in the opening to define a second loop 24' that is interlaced with the first loop 24 to define a releasable joint 10. When the release member 50 is in a first position (FIG. 3), the release member inhibits a) travel of the first coupling member 25 through the second loop 24' and b) travel of the second coupling member 25' through the first loop 24, thereby attaching the first and second elongated elements 20, 20' to each other. Furthermore, movement of the release member 50 from the first position into a second position (FIG. 4) different than the first position does not inhibit a) travel of the first coupling member 25 through the second loop 24' and b) travel of the second coupling member 25' through the first loop 24, thereby detaching the first and second elongated elements 20, 20' from each other.

Referring back to FIGS. 1-5, the elongated elements 20, 20' are illustrated as sutures, which are suitable for implantation in human and/or animal tissue. The first terminal end 35 can connect to a structure, such as an implant or tissue (such a bone, ligaments, tendons, vessels, etc.) and the second terminal end 35' can connect to a surgical instrument or other device. In one example, the device may be a vascular closure device configured to plug a hole in a vessel. Such a vascular closure device is similar to that disclosed in WO Publication No. 2015/099977, the entire disclosure of which incorporated by reference into the present application. Each suture is elongate along a respective central axis, and each coupling member has a cross-sectional dimension that is perpendicular to the respective central axis and is greater than a cross-sectional dimension of the respective suture. The cross-sectional dimension of the respective suture is perpendicular to the respective central axis. Each suture can be a multifilament suture, a monofilament suture, or a braided suture. Furthermore, each suture has a United States Pharmacopeia size between #11-0 to #7. In one example, each suture has a United States Pharmacopeia size of #11-0. In another example each suture has a United States Pharmacopeia size of #10-0. In one example, each suture has a United States Pharmacopeia size of #9-0. In one example, each suture has a United States Pharmacopeia size of #8-0.

In another example each suture has a United States Pharmacopeia size of #7-0. The suture size is not limited to #11-0 to #7.

The releasable elongated assembly can be used in remote suturing, orthopedic surgery, and with vascular closure devices, as discussed above. For remote suturing, the suture length and length of the release member are extended, which prohibits simple cutting of the suture to release. The releasable elongated assembly would allow separation of two length of suture connected at a point located inside tissue without the need for using a cutting instrument. In one example of a surgical application, the first suture extends out of the first end of the release member 50 and is attached to an instrument, and the second suture extends out of the second end of the release member 50 and is attached to an implant configured to be implanted into tissue. In another example of a surgical application, either the first suture or the second suture is attached to a vascular closure device configured to seal a puncture in a vessel. In another example of a surgical application, either the first suture or the second suture is attached to a needle configured to guide the respective suture through tissue.

The releasable assembly can be also be applied to non-surgical applications, such as outdoor equipment (tenting), ropes, awnings, nautical applications, and fishing equipment. In one example, either the first elongated element or the second elongated element is attachable to a first structure and the other of the first elongated element or the second elongated element is attachable to a second structure so as to couple the first structure to the second structure. The first and second structures can be any particular structure, such a tent, boat, nautical components on a boat, fishing equipment, etc. In another example, the first elongated element and the second elongated element can be attached to a structure to define a releasable loop when the assembly is in an attached configuration.

What is claimed:

1. A releasable elongated assembly comprising:
   a release member including an elongate opening;
   a first elongated element having a first coupling member;
   a second elongated element having a second coupling member releasably couplable with the first coupling member, wherein:
   the first elongated element defines a first loop adjacent to the first coupling member,
   the second elongated element defines a second loop, and
   when the first coupling member and the second coupling member are received in the elongate opening, the release member inhibits release of the first and second coupling members from one another.

2. The releasable elongated assembly of claim 1, wherein the first elongated element is folded in the elongate opening, and the second elongated element is folded in the elongate opening such that the second loop is interlaced with the first loop.

3. The releasable elongated assembly of claim 2, wherein the release member inhibits:
   travel of the first coupling member through the second loop; and
   travel of the second coupling member through the first loop.

4. The releasable elongated assembly of claim 1, wherein the elongate opening has a dimension sized such that the first and second coupling members are inhibited from travel past each other in the elongate opening.

5. The releasable elongated assembly of claim 1, wherein the release member includes a first end and a second end opposite the first end, wherein the first elongated element extends out of the first end, and the second elongated element extends out of the second end.

6. The releasable elongated assembly of claim 1, wherein either the first elongated element or the second elongated element is attachable to a first structure and the other of the first elongated element or the second elongated element is attachable to a second structure so as to couple the first structure to the second structure.

7. The releasable elongated assembly of claim 1, wherein the first loop of the first elongated element and the second loop of the second elongated element together define a releasable loop.

8. The releasable elongated assembly of claim 1, wherein each elongated element is one of a cord, a rope, a plied strand, a monofilament strand, a multifilament strand, a braid, a wire, a cable, or a suture.

9. The releasable elongated assembly of claim 1, wherein the first and second coupling members are first and second knots.

10. The releasable elongated assembly of claim 1, wherein the first and second coupling members are the first and second coupling bodies attached to the respective first and second elongated elements.

11. The releasable elongated assembly of claim 1, wherein when the first coupling member and the second coupling member are removed from the elongate opening, the first and second coupling members are releasable from one another.

12. A suture assembly, comprising:
    a release member including a lumen;
    a first suture having a first coupling member;
    a second suture having a second coupling member releasably couplable with the first coupling member, wherein:
    the first suture defines a first loop adjacent to the first coupling member,
    the second elongated element defines a second loop, and
    when the first coupling member and the second coupling member are received in the lumen, the release member inhibits release of the first and second coupling members from one another.

13. The suture assembly of claim 12, wherein the first suture is folded in the lumen, and the second suture is folded in the lumen such that the second loop is interlaced with the first loop.

14. The suture assembly of claim 12, wherein the release member includes a first end and a second end opposite the first end, and the lumen extends from the first end to the second end.

15. The suture assembly of claim 14, wherein the first suture extends out of the first end of the release member and is attachable to an instrument.

16. The suture assembly of claim 14, wherein the second suture extends out of the second end of the release member.

17. The suture assembly of claim 12, wherein the first and second coupling members are at least one of first and second knots formed in the respective first or second sutures or first and second coupling bodies attachable to the respective first and second sutures.

18. The suture assembly of claim 12, wherein the release member inhibits:
    travel of the first coupling member through the second loop; and travel of the second coupling member through the first loop.

19. The suture assembly of claim 12, wherein the lumen has a dimension sized such that the first and second coupling members are inhibited from travel past each other in the lumen.

20. A releasable elongated assembly comprising:
a release member including an elongate opening;
a first elongated element having a first coupling member;
a second elongated element having a second coupling member releasably couplable with the first coupling member, wherein the first elongated element is folded in the elongate opening to define a first loop adjacent to the first coupling member, and the second elongated element is folded in the elongate opening to define a second loop interlaced with the first loop.

* * * * *